(12) United States Patent
Wang

(10) Patent No.: US 6,789,474 B2
(45) Date of Patent: Sep. 14, 2004

(54) WATER CONTENT SENSING SYSTEM FOR INK/WATER EMULSION OF LITHOGRAPHIC PRINTER

(75) Inventor: Xinxin Wang, Naperville, IL (US)

(73) Assignee: Goss International Corporation, Westmont, IL (US)

( * ) Notice: Subject to any disclaimer, the term of this patent is extended or adjusted under 35 U.S.C. 154(b) by 0 days.

(21) Appl. No.: 10/219,830

(22) Filed: Aug. 15, 2002

(65) Prior Publication Data

US 2003/0033946 A1 Feb. 20, 2003

Related U.S. Application Data

(60) Provisional application No. 60/313,628, filed on Aug. 20, 2001.

(51) Int. Cl.[7] ........................... B41L 23/00; G01R 27/26
(52) U.S. Cl. ....................... 101/147; 324/658; 324/664; 324/689; 324/694
(58) Field of Search ................................ 324/694, 658, 324/678, 662, 707, 664, 601, 681, 689, 693; 101/147, 364, 365, 350.1; 73/304 C

(56) References Cited

U.S. PATENT DOCUMENTS

| | | | |
|---|---|---|---|
| 4,388,864 A | | 6/1983 | Warner |
| 4,559,493 A | | 12/1985 | Goldberg et al. |
| 4,658,207 A | | 4/1987 | Scribano et al. |
| 4,690,055 A | | 9/1987 | Fadner et al. |
| 4,864,925 A | | 9/1989 | Van Kanegan et al. |
| 4,916,940 A | * | 4/1990 | Mougne ..................... 73/61.43 |
| 5,044,274 A | | 9/1991 | Gaunt |
| 5,389,884 A | * | 2/1995 | Nakamura et al. .......... 324/663 |
| 5,791,249 A | | 8/1998 | Quadracci |
| 5,927,200 A | | 7/1999 | Chou et al. |
| 5,945,831 A | * | 8/1999 | Sargent et al. .............. 324/686 |
| 6,086,064 A | * | 7/2000 | Biegelsen et al. ..... 271/258.01 |
| 6,169,407 B1 | | 1/2001 | Wang et al. |
| 6,176,138 B1 | * | 1/2001 | Barr et al. .................... 73/756 |
| 6,237,412 B1 | * | 5/2001 | Morimoto ................. 73/304 C |
| 6,255,954 B1 | * | 7/2001 | Brown et al. ............... 340/603 |
| 6,269,693 B1 | * | 8/2001 | Irion ......................... 73/304 C |
| 6,380,750 B1 | * | 4/2002 | Schenck, Jr. et al. ........ 324/690 |
| 6,397,745 B2 | * | 6/2002 | Koehler ....................... 101/366 |
| 6,401,612 B2 | * | 6/2002 | Koehler ....................... 101/365 |
| 6,524,452 B1 | * | 2/2003 | Clark et al. ................. 204/254 |
| 6,539,797 B2 | * | 4/2003 | Livingston et al. ....... 73/304 C |
| 2002/0186270 A1 | * | 12/2002 | Sharma ....................... 347/28 |

OTHER PUBLICATIONS

Peter M B Walker, Chambers Dictionary of Science and Technology, General Edition, p. 650.*
PCA40—40mm Flat–Pack, Analog Proximity Sensor w/expandalbe sensor, http://www.gordonproducts.com/PCA40.htm 2 pages (1998).
Specifications for PCA40—40mm Flat–Pack, Capacitive Analog Sensor w/voltage output, http://www.gordonproducts.compca40_specs.htm 3 pages (1998).

* cited by examiner

Primary Examiner—Andrew H. Hirshfeld
Assistant Examiner—Wasseem H. Hamdan
(74) Attorney, Agent, or Firm—Marshall, Gerstein & Borun LLP

(57) ABSTRACT

A printing press system with water content sensing capability is disclosed. Many printing operations, including keyless or lithographic printing presses, use an emulsion of ink and water to perform the printing operation. It is important that the emulsion maintain a proper balance between the ink and water. The disclosed system employs a sensor which may be placed in the ink train of the printing press to constantly monitor the level of water within the emulsion. The sensor may be a capacitive type sensor which detects changes in the dielectric constant of the emulsion, and based on a comparison of the measured value and a predetermined desired value, prompts the press operator regarding the imbalance to enable corrective action to be taken.

12 Claims, 2 Drawing Sheets

WATER CONTENT SENSING SYSTEM FOR INK/WATER EMULSION OF LITHOGRAPHIC PRINTER

RELATED APPLICATIONS

The present application claims priority from provisional application Ser. No. 60/313,628, filed on Aug. 20, 2001.

FIELD OF THE DISCLOSURE

The disclosure generally relates to printing processes and, more particularly, relates to lithographic printing.

BACKGROUND OF THE DISCLOSURE

Lithographic printers typically employ two liquids, i.e., an ink and a fountain solution, in conducting the printing process. The ink covers an image area of a lithographic plate to produce text and graphics on the paper being printed. The fountain solution, which is a water-based chemical solution, covers the non-image areas of the plate to keep the rest of the paper free from being printed with ink.

During the printing process, the ink is mixed with the fountain solution producing an ink/water emulsion. The balance between the two liquids needs to be accurately maintained for proper printing to occur. If the water content in the emulsion becomes too high or too low, the print quality will be degraded. Ink and water balancing in the emulsion is especially important for a keyless printing press, where unused ink is scraped off a scraping roller of an ink train and re-circulated to the ink applicator through one or more ink hoses or conduits. Since the diameter of a typical ink hose is relatively small, e.g., about eight millimeters, proper ink and water balancing is also important to, among other things, ensure proper viscosity in the emulsion and thus adequate flow through the conduit.

SUMMARY OF THE INVENTION

In accordance with one aspect of the disclosure, a water sensor for a lithographic printing press is provided which includes an enclosure having an emulsion input and an emulsion output, a chamber extending through the enclosure and fluidically connecting the input to the output, and a capacitive sensor mounted in the enclosure proximate the chamber.

In accordance with another aspect of the disclosure, a printing press is provided which includes a frame, a plurality of rollers adapted to traverse a web of paper through the frame to be printed, an ink train adapted to carry an ink/water emulsion to at least one print roller, a water content sensor in fluid communication with the ink/water emulsion, and an operator interface device in electrical communication with the water content sensor.

These and other aspects and features of the disclosure will become more apparent from the following detailed description when taken in conjunction with the accompanying drawings.

Figure 1:
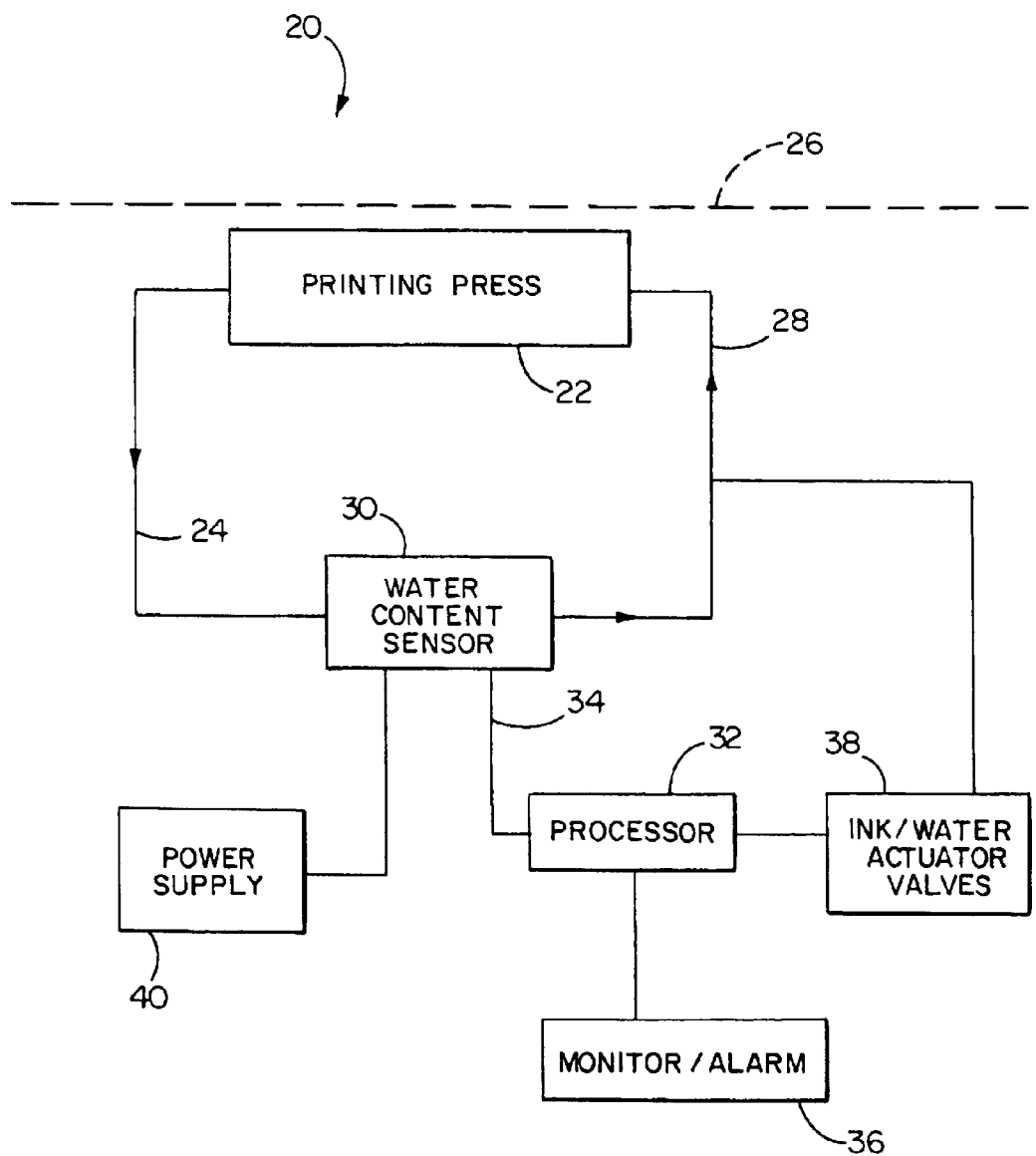
FIG. 1 is a schematic representation of a printing press with water sensing capability as constructed in accordance with the teachings of the disclosure.

While the disclosure is susceptible to various modifications and alternative constructions, certain illustrative embodiments thereof have been shown in the drawings and will be described below in detail. It should be understood, however, that there is no intention to limit the invention to the specific forms disclosed, but on the contrary, the intention is to cover all modifications, alternative constructions and equivalents falling within the spirit and scope of the invention as defined by the appended claims.

DETAILED DESCRIPTION OF THE DISCLOSURE

Referring now to the drawings, and with specific reference to FIG. 1, a printing press with water content sensing capability constructed in accordance with the teachings of the disclosure is generally referred to by reference numeral 20. While the system 20 will be described in conjunction with reference to a lithographic printing process, it is to be understood that the teachings of the disclosure can be used to detect, sense, and measure water content levels in a variety of other types of mixed solutions, in printing as well as other industries, including but not limited to, paints and stains, chemical processing, petroleum refineries, and the like.

The system 20 includes a printing press 22 which employs an ink and water emulsion 24 for printing upon a moving web of paper 26. In a typical lithographic printing process, a keyless printing press is employed which uses an ink train 28 to direct the emulsion 24 to and from the printing press 22. The ink train 28 further includes a plurality of rollers (not shown) for directing excess ink back through the ink train 28 for recycling. It is to be understood that the details of such an ink train as well as the doctor blades used to remove ink from the ink train and the particulars of the actual printing press 22, are not disclosed in this application. The assignee has a large number of issued U.S. Patents directed to such technology, some of which are U.S. Pat. Nos. 5,806,427; 5,868,071; and 5,943,955, each of which are herein incorporated by reference.

In such a keyless printing system 20, the ink train 28 includes hoses or conduit for directing the water/ink emulsion 24 removed by a doctor or scraping blade back to an inker or applicator at the beginning of the ink train for recycling. A water content sensor 30 constructed in accordance with the teachings of the disclosure may be provided within such a conduit. It is to be understood that the water sensor 30 need not be disposed within the conduit but can be placed anywhere in the system in fluid communication with the emulsion 24. In so doing, the water content level within the water and ink emulsion 24 can be continuously monitored and balanced. If the water content level falls outside desired operating parameters, such an event can be detected and corrective action can be taken. It is to be further understood that the water sensor 30 can be used with equal efficiency with direct printing operations in addition to such offset printing operations.

More specifically, it will be noted that the system 20 further includes a processor 32 in electric communication with the water sensor 30. The water sensor 30, as will be described in further detail herein, directs a signal 34, such as an analog signal, to the processor 32. The processor 32 compares the signal 34 to the desired value for the water content level stored in memory. If the comparison detects an imbalance or error, a number of actions can be taken, some of which include the actuation of an alarm 36 as by a computer or the like. Alternatively, or in conjunction with, such an alarm, the processor 32 can activate a valve or plurality of valves 38 to increase or decrease the percentage of ink and/or water provided within the emulsion 24 to return the emulsion 24 to within a correct operating range. Also shown in FIG. 1 is a power supply 40 connected to the water sensor 30.

Figure 2:
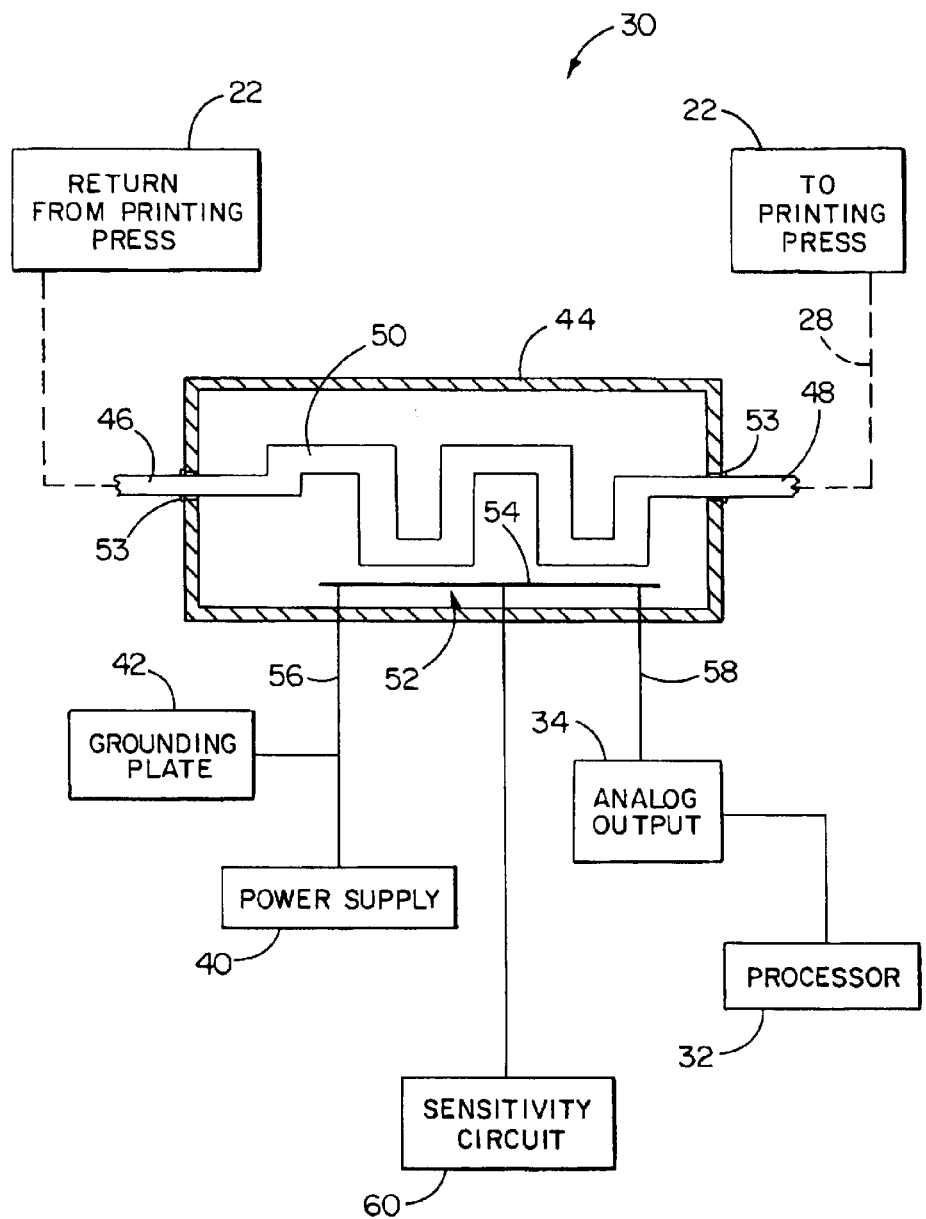
FIG. 2 is a schematic, partial sectional view of a water content sensor constructed in accordance with the teachings of the disclosure.

Referring now to FIG. 2, the water content sensor 30 is shown in further detail. As shown therein, the sensor 30 includes an exterior housing or enclosure 44 having an emulsion inlet 46 as well as an emulsion outlet 48.

In the enclosure 44 are a chamber 50 connecting the inlet 46 to the outlet 48, as well as a sensing device 52. The enclosure 44 is preferably manufactured from metal to, among other things, prevent any surrounding objects or devices from affecting the accuracy and measurement of the sensing device 52. The inlet 46 and outlet 48 are also preferably sealed as by gaskets 53 to prevent any unwanted emulsion 24 from escaping, and to prevent any unwanted liquid from gaining access into the enclosure 44. The chamber 50 is preferably manufactured from a non-conductive material with a low dielectric constant, such as Teflon®, or PVC (polyvinylchloride) plastic.

The sensing device 52 is preferably a capacitive sensor which includes a sensing surface 54, a power input 56, an analog output 58, a grounding plate 42, and a sensitivity mechanism 60. It will be noted that the grounding plate 42 is electrically connected to the metal enclosure 44 and the common lead of the power input 56.

Such a capacitive sensor produces a voltage or current output signal 34 which is proportional to the capacitance between the sensing surface 54 and the grounding plate 42. As the percentage of water within the emulsion 24 increases, the capacitance of the emulsion 24 increases as well, as measured by a dielectric constant. Accordingly, if the capacitance or dielectric constant of the emulsion 24 increases, the percentage of water within the emulsion 26 is known to be increasing as well. A typical type of capacitive sensor which may be utilized by the system 20 is a capacitive sensor made by Gordon Products under model no. PCA40.

In order to optimize the sensing capability of the device 52, a number of steps may be taken. For example, the sensing surface 54 is preferably located or positioned as close to the chamber 50 as possible. Moreover, the chamber 50 itself is preferably configured to provide a relatively great surface area, thereby exposing the emulsion 24 to the sensing surface 54 to a greater degree. Both features combine to result in better readings and accuracy within the sensing device 52. In the depicted embodiment, the chamber 50 increases its exposed surface area by employing a labyrinthine pathway directing the emulsion 24 from the inlet 46 to the outlet 48. In alternative embodiments, a plurality of such pathways or chambers 50 can be employed to further increase the exposed surface area.

In order to decrease the resistance to flow of the emulsion 24 through the sensor 30, it is desirable to construct the chamber 50 to have a cross-sectional area slightly larger than that of the inlet 46 and outlet 48.

In operation, and by way of example, the nominal value of the dielectric constant of water is about eighty. Such a value is significantly higher than the dielectric constant of most ink, which typically has a dielectric constant of less than ten. When the water content within the emulsion increases, the dielectric constant of the emulsion 24 increases accordingly. Thus, the output of the capacitive sensing device 52 can be used to detect the water content in the ink/water emulsion 24. To optimize the measurement, the size of the enclosure 44 and the distance between the sensing surface 54 and the chamber 50 should be carefully selected. It is preferable that when the chamber 50 is empty, the sensor produces a very low signal, i.e., about 0.5 volts, to prevent the sensor 30 from being under biased. The low output voltage also provides a mechanism for detecting an unconnected sensor. The 0.5 volt output voltage can be achieved by adjusting the sensor's sensitivity, as by the tunable gain circuit or sensitivity adjustment mechanism 60. Some emulsion 24 can carry as high as 45% water. Therefore, the spacing between the sensing surface 54 and the chamber 50, and the gain of the sensor 30, should be designed to ensure that the sensor output signal 34 is accurate.

The sensor output signal 34 can be calibrated to reflect the true water content in the emulsion 24. This can be accomplished by using, for example, pre-mixed emulsions with known water contents. Since different inks have different compositions, their dielectric constant may vary slightly. To ensure the accuracy of the measurement, the sensor 30 can be calibrated with the type of ink used in the particular printing process. It has been noticed by the inventors that when the water content value is above 20%, the dielectric constant of an ink/water emulsion is mainly determined by the amount of water contained. The variation of dielectric constants of the inks becomes a relatively insignificant factor in such a situation. Glycerin is a colorless liquid with a nominal dielectric constant of about 42 and can be used for such calibration purposes. Among other benefits, glycerin is a stable, environmentally sound, material which does not harm the sensor and allows for easy cleaning of the sensor after calibration. It is to be understood that materials other than glycerin can be employed for the purpose of calibration as well.

The sensor 30 is energized by the power supply 40. The common lead of the power supply 40 is also connected to the grounding plate 42 for safety and noise reduction reasons. The output of the sensor 30 can be connected to the processor 32 through a communication network or otherwise. The processor 32 preferably converts the sensor signal 34 into the water content by a mapping function stored in memory. More specifically, a reference table or the like may be stored in memory, such that if the measured capacitance is known, the corresponding water content can be identified as well. The processor 32 can, among other things, display the water content value on the monitor 36, prompt the press operator when the water content is higher than a predetermined level, sound an alarm, or actuate the valve 38 to correct the situation. The readings and operating data monitored can be stored in memory for historical logging and troubleshooting purposes.

From the foregoing, it will be understood by one of ordinary skill in the art that the teachings of the invention can be used to construct a system and water content sensor to provide press operators an early warning before the ink and water emulsion becomes unbalanced. Such a system accordingly improves print quality and reduces waste.

What is claimed is:

1. A water sensor for a lithographic printing press, comprising:
an enclosure including an emulsion input and an emulsion output;
a capacitive sensor mounted in the enclosure for sensing the amount of water in the emulsion; and
a chamber extending through the enclosure and fluidically connecting the emulsion input to the emulsion output; the chamber forming a fluid pathway having a plurality of regions positioned proximate the sensor to provide multiple passes of the fluid across a sensing area of the sensor.

2. The sensor of claim 1, the capacitive sensor including a sensing surface.

3. The sensor of claim 2, further including a power supply for the capacitive sensor and a grounding plate.

4. The sensor of claim 3, the capacitive sensor being adapted to produce an analog voltage proportional to the capacitance between the sensing surface and the grounding plate.

5. The sensor of claim 4, further including a processor receiving the analog voltage.

6. The sensor of claim 5, the chamber further including a water/ink emulsion.

7. The sensor of claim 6, the processor being adapted to convert the analog voltage into a water content of the water/ink emulsion.

8. The sensor of claim 1, the chamber being manufactured from a material with low electrical conductivity.

9. The sensor of claim 8, the chamber being manufactured from polyvinylchloride.

10. The sensor of claim 1, the chamber having a larger cross-sectional area than the emulsion input.

11. The sensor of claim 1, the chamber further including a plurality of pathways.

12. The sensor of claim 1, the enclosure being manufactured from a metal.

* * * * *

UNITED STATES PATENT AND TRADEMARK OFFICE
CERTIFICATE OF CORRECTION

PATENT NO.  : 6,789,474 B2
DATED       : September 14, 2004
INVENTOR(S) : Xinxin Wang It is certified that error appears in the above-identified patent and that said Letters Patent is hereby corrected as shown below:

Column 4,
Line 66, please delete "output; the" and insert -- output, the --.

Column 5,
Line 9, please delete "produce" and insert -- product --.

Signed and Sealed this

First Day of February, 2005

JON W. DUDAS
*Director of the United States Patent and Trademark Office*